United States Patent [19]

Rescalli et al.

[11] Patent Number: 5,756,866
[45] Date of Patent: May 26, 1998

[54] PROCESS FOR OBTAINING SEPARATE STREAMS OF METHANOL AND ETHANOL, N-PROPANOL AND ISOBUTANOL

[75] Inventors: Carlo Rescalli; Ugo Melis, both of San Donato Milanese, Italy

[73] Assignee: Agip Petroli S.p.A., Rome, Italy

[21] Appl. No.: 569,962

[22] Filed: Dec. 8, 1995

[30] Foreign Application Priority Data

Dec. 21, 1994 [IT] Italy .................... MI94A2586

[51] Int. Cl.$^6$ .......................... C07C 27/26; C07C 29/80; B01D 3/00; B01D 1/02
[52] U.S. Cl. ...................... 568/913; 203/20; 203/18; 203/78
[58] Field of Search ................ 568/913; 203/20, 203/18, 78

[56] References Cited

U.S. PATENT DOCUMENTS 4,645,570  2/1987  Sridahr .

5,449,440  9/1995  Rescalli et al. .

FOREIGN PATENT DOCUMENTS 2103489   5/1994   Canada .
0306358   3/1989   European Pat. Off. .
2203148   10/1988  United Kingdom .

*Primary Examiner*—Marianne M. Cintins
*Assistant Examiner*—Karl J. Puttlitz, Jr.
*Attorney, Agent, or Firm*—Rogers & Wells; George P. Hoare

[57] ABSTRACT

The process claimed enables three separate streams to be obtained, from mixtures containing methanol, ethanol, n-propanol, isobutanol, water and other both low- and high-boiling compounds, of which one is anhydrous basically consisting of methanol and ethanol (I), one containing most of the n-propanol present in the mixture fed (II), together with small quantities of methanol, ethanol, isobutanol and water, and one containing most of the isobutanol and high-boiling compounds present in the above mixture (III), by the use of three rectifying columns, stream (I) being taken from a lateral point of the first column, stream (II) obtained from the head of the second column, stream (III) obtained from the bottom of the second column.

13 Claims, 1 Drawing Sheet

PROCESS FOR OBTAINING SEPARATE STREAMS OF METHANOL AND ETHANOL, N-PROPANOL AND ISOBUTANOL

The present invention relates to a process for obtaining separate streams of methanol and ethanol, n-propanol, isobutanol starting from mixtures of these with water and other both high- and low-boiling organic compounds.

These mixtures can be produced (in the presence of suitable catalysts by operating in the appropriate T and P ranges) from synthesis gases obtained by the partial oxidation of methane or naphtha, by the steam reforming of methane or gasification of carbon; they can be used in the synthesis of methyl and ethyl ethers (MTBE and ETBE) with a high octane number, products which are of increasing interest due to the recent regulations relating to fuels, owing to their octane characteristics and content of oxygen.

As market demands for MTBE are becoming more and more hindered by the difficulty of synthesis via the addition of methanol to isobutene present in $C_4$ streams from Steam Cracking (S.C.) and Fluid Catalytic Cracking (F.C.C.), due to a scarcity of isobutene itself, the use of mixtures of alcohols obtained from CO and $H_2$ which can be sources of isobutene, has become particularly interesting, if the isobutanol contained therein is separated and dehydrated to olefin: in this way the alcohol mixtures become a source of both the raw materials necessary for the production of MTBE and ETBE or of the mixtures themselves, thus becoming a strategic alternative to the classical production of these compounds from S.C. and F.C.C.

To make the synthesis of products with a high octane number such as MTBE and ETBE from mixtures obtained from CO and $H_2$ of economical interest, streams must be available which satisfy certain requisites, such as:

the methyl and ethyl alcohols can be also be mixed with each other, but always with a low level of water; the level of $C_3$ alcohol must be minimum therein as the latter reacts with iso-olefins with a not very favourable thermodynamics, also generating products of little interest from an octane point of view.

the propyl alcohol is preferably recycled to the synthesis reactor of alcohols from CO and $H_2$ as it causes an increase in the production of isobutanol, an alcohol which is of great interest as it is a source of isobutene. The stream rich in propanol, which is recycled to the synthesis reactor of alcohols, must be marked by a relatively low water content but can on the other hand be marked by relatively high quantities of other alcohols among which methanol and ethanol; the former is in fact recovered as CO and $H_2$ whereas the second is transformed into isobutanol and consequently into a more valuable product.

the isobutyl alcohol (and other high-boiling products possibly present) sent for dehydration to obtain isobutene must have a negligible content of light $C_2$ and $C_3$ alcohols to avoid the production of light non-etherifiable olefins with the catalytic system normally used in etherification to MTBE and ETBE, which are in any case of no interest. Viceversa, in this stream the presence of high-boiling products (oxygenated or not) is accepted.

The separation cycle of the present invention relates to a process which satifies all of the above conditions.

The separation of water is usually difficult and onerous particularly because of the formation of binary azeotropes or multicomponents of this with n-propanol and isobutanol, both of the homogeneous and heterogenous type.

The normal technique suggests separating the methanol and ethanol at the head of the first column, subsequently the water by azeotropic distillation carried out in the presence of a suitable additive called entrainer (with the use of two columns) and then the propanol with a subsequent rectifying column (the isobutanol remains at the bottom of the first column): this cycle entails extremely high investment and operating costs mainly due to the separation of the water.

A process has recently been claimed (with patent application IT-MI92-A002658) which allows three separate streams to be obtained, from mixtures containing methanol, ethanol, n-propanol, isobutanol, water and other low- and high-boiling compounds, of which one is anhydrous basically consisting of methanol or methanol and ethanol, one containing most of the n-propanol present in the mixture fed, one containing most of the isobutanol present in the above mixture, the first stream being taken from an upper side point of the first column, the second stream obtained from the head of the second column, the third stream obtained from the bottom of the second column.

The process described in the above Italian application enables all the goals to be reached, operating however with a much simpler method (three rectifying columns of which one of limited dimensions) and with considerably lower operating costs compared to those of the cycle suggested above by the prior art.

A process has now been found which entails a simple operating method as that described in the Italian application and consequently with more or less the same investment and operating costs, from which, not only an anhydrous stream basically consisting of methanol and ethanol and a stream containing most of the isobutanol present in the mixture fed, are obtained, but also a stream containing most of the n-propanol present in the above mixture with a much lower water content however, which obviously favours further use of this stream.

The process of the present invention, with which three separate streams are obtained, of which one anhydrous basically consisting of methanol and ethanol (I), one containing most of the n-propanol present in the mixture fed, together with small quantities of other alcohols and water (II), one containing most of the isobutanol and other high-boiling compounds contained in the mixture fed (III), starting from a mixture containing from 20 to 80% by weight of methanol, preferably from 35 to 70%, from 0.1 to 10% by weight of ethanol, preferably from 0.1 to 5%, from 0.1 to 20% by weight of n-propanol, preferably from 1 to 10%, from 2 to 40% by weight of isobutanol, preferably from 10 to 30%, from 0.1 to 50% by weight of water, preferably from 1 to 10%, the complement to 100 basically consisting of other organic compounds, both low- and high-boiling, of an alcoholic nature (such as isopropanol, n-butanol, etc.) or of a different nature (oxygenated products such as ethers, esters, ketones, aldehydes, acids, heterocyclic products, etc. and/or non-oxygenated products such as saturated, unsaturated, aromatic hydrocarbons, etc.), is characterized in that it comprises the following steps:

feeding the above mixture to a first rectifying column discharging at the head a stream basically consisting of the inert products and low-boiling compounds, removing from a side point situated above the feeding the anhydrous liquid stream (I) basically consisting of methanol and ethanol, removing from a side point below the feeding a liquid stream which, after cooling, is separated into two phases, one aqueous and the other organic, the latter being recycled to an intermediate point immediately below the removal point mentioned above, and obtaining from the bottom a liquid stream basically containing all the n-propanol, isobutanol and other high-boiling compounds, possibly with small quantities of methanol and ethanol contained in the mixture fed;

feeding the stream obtained from the bottom of the first rectifying column to a second rectifying column obtaining at the head the stream (II) containing most of the n-propanol contained in the mixture fed, together with small quantities of methanol, ethanol, isobutanol and water, and obtaining at the bottom the stream (III) containing most of the isobutanol and high-boiling compounds contained in the mixture fed;

feeding the aqueous phase generated by separating the liquid stream removed from the lower lateral point of the first rectifying column, to a third rectifying column, recovering at the head the alcohols and other organic compounds contained there, which are preferably recycled to the first column, and discharging from the bottom a stream basically consisting of water, the pressures at which the above columns and separator operate being selected within a range of between 30 and 500 absolute KPascals, preferably between 100 and 300.

An antifoam solution such as, for example, an aqueous siliconic mixture can be sent into the first rectifying column (preferably in a point immediately below the side removal point of the stream (I) and/or into the second rectifying column (preferably in the liquid phase of the condenser).

The cooling and separating of the liquid stream removed from the lower side point of the first rectifying column enables (at practically no cost) the initial removal of most of the water fed to the column with a consequently significant saving of investment and operating costs of the whole complex involved (the separation of the water is completed with the third column whose costs are extremely reduced).

The stream (III) is practically without n-propanol and can be used to generate, by dehydration in the presence of a suitable catalyst, isobutene (and other heavier olefins) to be used, together with the stream (I) of methanol and ethanol, for producing MTBE and ETBE.

In the event that the effluent from the alcohol synthesis reactor is marked by the presence of relatively high concentrations of by-products of the aldehyde, ketone and acid type, this stream can be advantageously subjected to hydrogenation before being sent to the separation cycle in question.

To totally eliminate traces of acid compounds the same stream or the stream discharged from the lower side removal point of the first column (before separation), can be sent to beds of basic ion exchange resins of various types (such as those marked by the presence of quaternary ammonic groups), or, alternatively, be treated with aqueous solutions of NaOH and/or other basic products such as carbonates, bicarbonates, phosphates of alkaline or earth alkaline metals and/or other basic compounds of the nitrogen containing type such as amines and/or alkanolamines.

The cycle can permit the production of isobutanol with a high titer (if required), even if the charge to the cycle is characterized by the presence of high concentrations of high-boiling compounds: it is sufficient to send the stream discharged from the bottom of the second column to an auxiliary rectifying column: isobutanol with a purity of >95% can be obtained from the head thereof.

Figure 1:
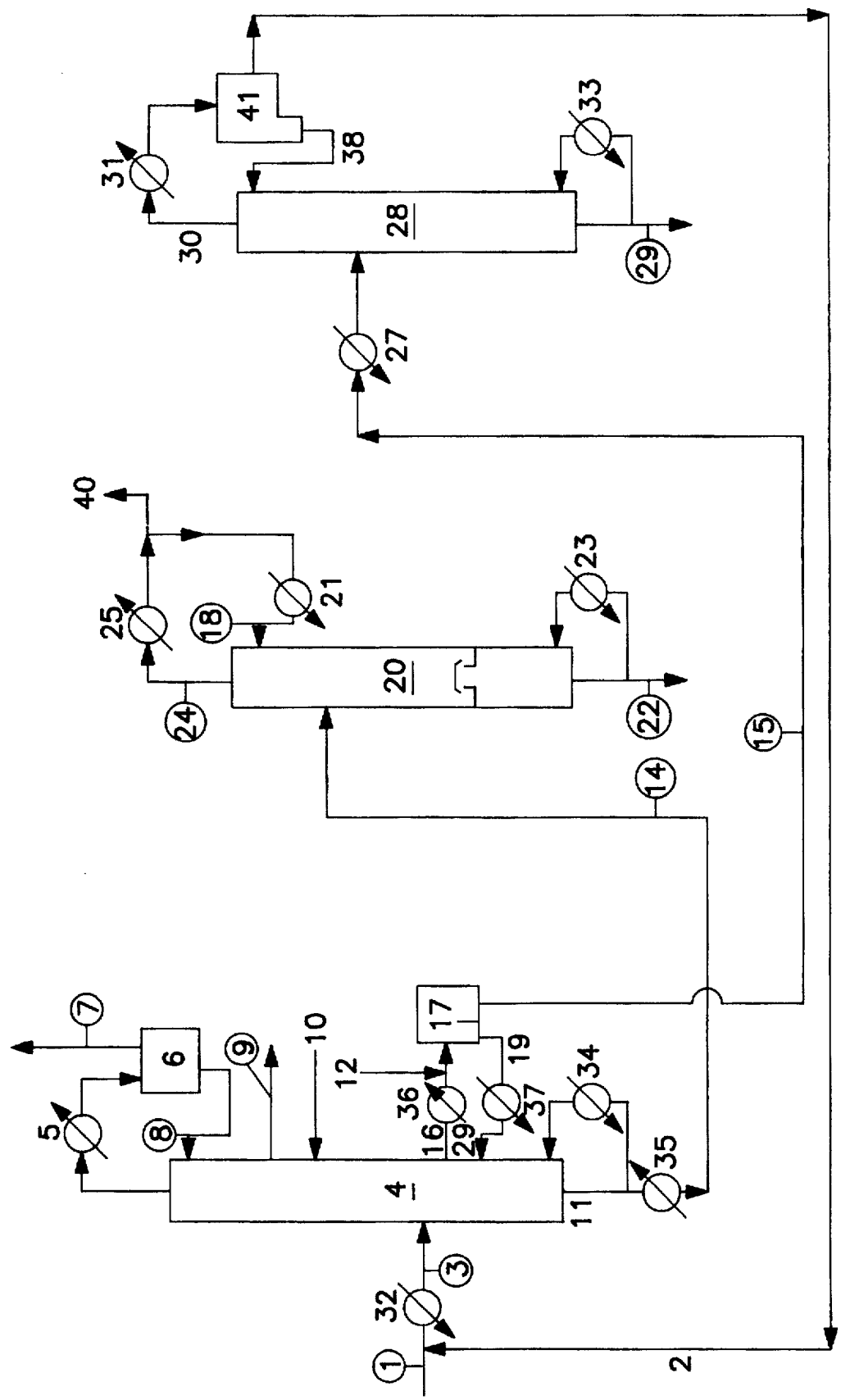
FIG. 1 represents a preferred but non-limiting embodiment of the invention itself and shows a rectifying process of the invention.

The mixture of alcohols, coming from the synthesis reactor, after being subjected to possible hydrogenation not shown in the figure, reaches the separation cycle via line 1 and together with the recycled stream 2 is preheated in 32 and via 3 to the rectifying column 4. After partial condensation in 5, the gaseous stream 7 leaves the reflux accumulator and is flushed to eliminate all the low-boiling compounds or those marked by analogous behaviour owing to the formation of low-boiling azeotropes (ethers, hydrocarbons, etc.); the liquid stream 8 discharged from the accumulator 6 is refluxed on the head plate (after possible preheating in an exchanger not shown). The anhydrous liquid stream of methanol and ethanol 9 is discharged from a plate of the column situated above the feeding; an antifoam solution is sent via line 10 immediately below line 9.

The liquid stream 16 discharged from a plate situated below the feeding is cooled in 36 and sent to the separator 17 in which an aqueous phase 26 and an organic phase 19 (mixture prevalently consisting of isobutanol and high-boiling products, saturated in water) are separated, the latter, preheated in 37 being recycled immediately below the removal plate of 16 to column 4 via line 29.

The stream leaving the bottom 11 (without methanol and ethanol) is discharged and after being cooled in 35 is fed to the second rectifying column 20.

The stream 24 discharged from the head, condensed in 25, is partially recycled to the alcohol synthesis reactor (line 40) and partially refluxed (line 18) after being preheated in 21; the stream 40 contains most of the propanol fed to the cycle, all the methanol and ethanol still present in 14 and small quantities of isobutanol: in this recycled stream the presence of water is accepted up to a few units per cent.

An aqueous solution of NaOH can be introduced via line 12, which neutralizes the acid compounds possibly present: the salts formed are eliminated by line 26.

Stream 22 consisting of isobutanol with small quantities of n-propanol and all the heavy compounds present in the charge is sent to a suitable reactor to be dehydrated to isobutene (the corresponding olefins can derive from other compounds present). Alternatively, this stream can be removed from the vapour phase of the reboiler (or a plate near it), to allow the high-boiling compounds to be flushed from the bottom with a consequent lengthening of the duration of the dehydration catalyst operating downstream: this alternative is not shown in the figure. (?)

The aqueous stream 26 is sent to the exchanger 27 and then to the final separation column 28 from the bottom of which stream 29, consisting only of water (possible presence of salts, if NaOH or other bases have been added from line 12 or other points of the cycle) is discharged; this stream can be sent to a classical water treatment plant to be definitely discharged. The stream at the head 30, after being condensed in 31, is partly refluxed via line 38 (after possible preheating in an exchanger not shown) and partly recycled to the feeding of the cycle for the recovery of the isobutanol and other alcohols contained in stream 26: the accumulator 41 is structured so as to allow in continuous the complete reflux of a possible aqueous phase present therein and guarantee recycling to the first column via 2 of the organic phase alone.

An example is provided which provides a better illustration of the present invention but does not limit its scope in any way.

EXAMPLE

The example is carried out in accordance with the diagram of FIG. 1.

Stream 3 (sum of stream 1 (effluent from the alcohol synthesis reactor) and stream 2 (recycled from 28)) consisting of:

|                 | Stream 1 g/h | Stream 2 g/h | Stream 3 g/h |
|-----------------|--------------|--------------|--------------|
| Low-boil. comp. | 9.0          | —            | 9.0          |
| Water           | 38.0         | 2.7          | 40.7         |
| Methanol        | 580.0        | —            | 580.00       |
| Ethanol         | 22.0         | —            | 22.0         |
| n-Propanol      | 65.0         | 3.2          | 68.2         |
| iso-Butanol     | 167.0        | 2.8          | 169.8        |
| high boil. comp.| 119.0        | 0.2          | 119.2        |
| Total           | 1000.0       | 8.9          | 1008.9       | is fed at T=55° C. to the first rectifying column 4 (Stage-type glass plated column, ⌀=50 mm, total plates=80, feeding point=45th plate from the bottom, head pressure= atmospheric, side removal point MeOH+EtOH=70th plate from the bottom).

A gaseous stream 7 of 10.0 g/h containing, together with other organic compounds, all the dimethylether present in the charge and small quantities of methanol (1.0 g/h) is discharged from the accumulator 6 at T=40° C.; the liquid phase 8 in equilibrium is refluxed at a flow rate of 2107 g/h.

The liquid stream discharged from the 70th plate (T≈69° C.) is characterized by:

|                |       | g/h | (>0.1% w/w) |
|----------------|-------|-----|-------------|
| Water <        | —     | g/h | (>0.1% w/w) |
| Methanol =     | 579.0 | "   |             |
| Ethanol =      | 22.0  | "   |             |
| Total =        | 601.0 | "   |             |

An aqueous solution containing 1% by weight of a siliconic antifoam agent (1.0 g/h—value not considered in the balance) is sent to the 69th plate.

The liquid phase present on the 5th plate above the reboiler is totally discharged, undercooled to 50° C. and then separated: whereas the resulting organic phase returns in continuous (after preheating to 80° C.) to the 4th plate, the aqueous phase consisting of:

|                    |      | g/h |
|--------------------|------|-----|
| Water =            | 37.9 | g/h |
| n-Propanol =       | 3.2  | "   |
| i-Butanol =        | 2.8  | "   |
| Heavy compounds =  | 0.2  | "   |
| Total              | 44.1 | "   | is sent to the column 28 for the recovery of the organic compounds and final separation of the water.

Stream 11 is discharged from the bottom (T≈102° C.) and is sent directly to the column 20 (plated column having the same characteristics as the previous one, operating at atmospheric pressure, with: total plates=70, feeding plate=45, operating pressure at head=atmospheric).

Streams 40 and 18, characterized as follows:

|           | (40) g/h | ← weight % → | (18) g/h |
|-----------|----------|--------------|----------|
| Water     | 2.8      | 4.1          | 22.4     |
| Methanol  | 0.0      | —            | —        |
| Ethanol   | 0.0      | —            | —        |
| Propanol  | 63.0     | 91.5         | 504.0    |
| i-Butanol | 3.0      | 4.4          | 24.0     |
| Total     | 68.8     | 100.0        | 550.4    | are recycled from the head of this column (T≈89° C.) to the alcohol synthesis reactor and column respectively.

Stream 22 consisting of:

|                     |       | g/h |
|---------------------|-------|-----|
| n-Propanol =        | 2.0   | g/h |
| i-Butanol =         | 164.0 | "   |
| Heavy compounds =   | 119.0 | "   |
| Total               | 285.0 | "   | is discharged from the bottom of column 20 (T≈120° C.).

Stream 26, preheated in 27 to T=80° C., is fed to the column 28 (plated column having the same characteristics as the previous ones, operating at atmospheric pressure, with 25 total plates and fed onto the 15th plate from the bottom).

The stream at the head 30 (T≈95° C.), after being condensed in 31 is partly refluxed, line 38 (26.7 g/h), and partly recycled to the inlet of the cycle via line 2 (8.9 g/h); the stream at the bottom 29 (35.2 g/h) consisting only of water, is eliminated.

We claim:

1. A process for obtaining three separate streams, one containing basically anhydrous liquid methanol and ethanol (I), one containing most of the n-propanol contained in the mixture fed, together with small quantities of other alcohols and water (II), one containing most of the isobutanol and other high-boiling compounds contained in the mixture fed (III), from a starting mixture containing from 20 to 80% by weight of methanol, from 0.1 to 10% by weight of ethanol, from 0.1 to 20% by weight of n-propanol, from 2 to 40% by weight of isobutanol, from 0.1 to 50% by weight of water, the complement to 100% basically consisting of other organic compounds, both low-and high-boiling, characterized in that it comprises the following steps:

(a) feeding the starting mixture to a first rectifying column and discharging at the head of the column a stream basically consisting of inert products and low-boiling compounds, removing from a first side point above the feeding of the starting mixture an anhydrous liquid stream basically consisting of methanol and ethanol (I), removing from a second side point below the feeding of the starting mixture a liquid stream which, after cooling, is separated into an aqueous phase and an organic phase, the organic phase being recycled to an intermediate point below the second side point, and obtaining from the bottom a liquid stream basically containing the n-propanol, isobutanol and other high-boiling compounds;

(b) feeding the stream obtained from the bottom of the first rectifying column to a second rectifying column and discharging at the head of the column a stream containing most of the n-propanol (II) contained in the mixture fed, together with small quantities of methanol, ethanol, isobutanol and water, and obtaining from the bottom a stream containing most of the isobutanol and high-boiling compounds (III) contained in the mixture fed; and (c) feeding the aqueous phase from the first rectifying column in step (a) to a third rectifying column, recovering at the head of the column the alcohols and other organic compounds contained therein, which are preferably recycled to the first column, and discharging from the bottom of the third rectifying column a stream basically consisting of water, wherein the pressures at which the rectifying columns operate are between 30 and 500 absolute KPascals.

2. The process according to claim 1 wherein the feeding mixture contains from 35 to 70% by weight of methanol, from 0.1 to 5% by weight of ethanol, from 1 to 10% by weight of n-propanol, from 10 to 30% by weight of isobutanol, from 1 to 10% by weight of water, the complement to 100% basically consisting of other organic compounds, both low-boiling and high-boiling.

3. The process according to claim 1 wherein the pressures at which the rectifying columns operate are between 100 and 300 absolute KPascals.

4. The process according to claim 1 wherein an antifoam solution is sent to the first rectifying column and/or to the second rectifying column.

5. The process according to claim 4 wherein the antifoam solution is sent to a point immediately below the first side point.

6. The process according to claim 4 wherein the antifoam solution is sent to the liquid phase of the condenser of the second rectifying column.

7. The process according to claim 1 wherein the stream (III) containing most of the isobutanol is removed from the vapour phase of the reboiler or a plate near this, whereas a liquid stream rich in high-boiling compounds is discharged from the bottom of the reboiler.

8. The process according to claim 1 wherein a solution of NaOH and/or other basic compounds such as carbonates, bicarbonates, phosphates of alkaline or earth-alkaline metals, and/or basic nitrogen containing compounds of the aminic and/or alkanolaminic type, is added to the starting mixture at the first rectifying column or to the stream removed from the lower side removal point of the first rectifying column.

9. The process according to claim 1 wherein the stream (III) is used to obtain isobutene by dehydration in the presence of a suitable catalyst.

10. The process according to claim 9 wherein the stream (I) is added to the isobutene produced by the dehydration of isobutanol to produce MTBE or mixtures of MTBE/ETBE.

11. The process according to claim 10 wherein part of the stream (I) is recycled to a reactor for the synthesis of alcohols from CO and $H_2$.

12. The process according to claim 1 wherein the stream (II) is recycled to a reactor for the synthesis of alcohols from CO and $H_2$.

13. A process according to claim 1 wherein the obtained bottom stream of the first rectifying column includes small quantities of methanol and ethanol contained in the mixture fed.

* * * * *